United States Patent [19]

Arai et al.

[11] Patent Number: 4,914,020

[45] Date of Patent: Apr. 3, 1990

[54] MULTI-LAYER ANALYTICAL ELEMENT WITH PRESERVED ENZYME CONTAINING SPREADING LAYER

[75] Inventors: Kazumi Arai, Hachioji; Mikio Koyama, Tokorosawa; Morio Kobayashi, Sagamihara; Kenichiro Okaniwa, Tokyo; Takasi Momose, Hino; Kunihiro Furukawa, Urawa; Souichi Zanma, Kawaguchi, all of Japan

[73] Assignees: Konishiroku Photo Industry Co., Ltd.; Chugai Seiyaku Kabushiki Kaisha, both of Tokyo, Japan

[21] Appl. No.: 824,450

[22] Filed: Jan. 31, 1986

[30] Foreign Application Priority Data

Feb. 5, 1985 [JP] Japan ................................. 60-19324

[51] Int. Cl.$^4$ .............................................. C12Q 1/00
[52] U.S. Cl. ........................................ 435/4; 435/11; 435/14; 435/15; 435/18; 435/19; 435/20; 435/23; 435/24; 435/25; 435/26; 435/28; 435/188
[58] Field of Search .............. 422/56; 436/810; 435/4, 435/23, 24, 188

[56] References Cited

U.S. PATENT DOCUMENTS

| | | | |
|---|---|---|---|
| 3,325,364 | 6/1967 | Merritt et al. | 435/188 |
| 3,344,028 | 9/1967 | Personeus et al. | 435/188 |
| 3,983,005 | 9/1976 | Goodhue et al. | 435/23 |
| 4,366,243 | 12/1982 | Rupchock et al. | 435/188 |
| 4,576,793 | 3/1986 | Koyama et al. | 422/56 |
| 4,657,739 | 4/1987 | Yasuda et al. | 435/4 |
| 4,671,937 | 6/1987 | Katsuyama et al. | 436/810 |

*Primary Examiner*—Sam Rosen
*Attorney, Agent, or Firm*—Frishauf, Holtz, Goodman & Woodward

[57] ABSTRACT

An analytical element to measure a specific component in a fluid samples comprising support, a layer containing a reagent provided the support and a spreading layer provided on above the reagent containing layer. In the spreading layer, an emzyme necessary for the reaction to produce a product capable of being detected with said reagent from the specific component is contained. The enzyme is protected from deterioration of activity during a manufacturing and preservation of the analytical element by means of the enzyme is included in the spread layer as a dispersion mixture with a protein and/or polypeptide. An accurate analytical result is stably obtained by the analytical element.

23 Claims, No Drawings

MULTI-LAYER ANALYTICAL ELEMENT WITH PRESERVED ENZYME CONTAINING SPREADING LAYER

FIELD OF THE INVENTION

The present invention relates to an analytical element containing enzyme catalyzing a reaction necessary for the measurement of an object to be tested and more particularly to an analytical element capable of maintaining the activity due to the coexistence of enzyme catalyzing the reaction needed in a measuring system and a substance inactive against aforesaid enzyme during the period of manufacturing and preserving of the analytical element.

BACKGROUND OF THE INVENTION

Many methods for analyzing specific components in fluid samples have hitherto been developed and these methods may be divided broadly into two types of a reaction system wherein reactions take place in a solution and a reaction system wherein reactions take place in a solid place carrier. A broad range including the method which does not use an instrument at all and is called a 'manual' method up to an automatic analyzing instrument is known as an analytical reaction in a solution system (hereinafter referred to as 'wet chemistry'). Especially in the field of clinical chemistry, its progress is remarkable and various kinds of quantitative analysis instruments for clinical chemistry have recently been introduced to clinical diagnostic loboratories of hospitals.

However, aforesaid methods have various disadvantages because reactions are basically made in the form of an aqueous solution in aforesaid methods. Namely, they cause an increase in energy consumption because they require much water, especially refined pure water or distilled water in the course of analysis. Further, various kinds of automatic analyzing instruments themselves are extremely expensive and require much skillfulness in the operation thereof and they not only require immense time and labor but also inevitably cause an environmental pollution with waste liquids therefrom. In contrast to aforesaid methods, analytical methods employing analytical reactions in solid phase system (hereinafter referred to as 'dry chemistry') are broadly used and they are performed in the form of a filter paper or the like containing reagent.

Aforesaid filter paper is prepared in a way wherein a water-absorbing fibrous carrier such as a filter paper is contained with reagent solution and then is dried as shown in U.S. Pat. No. 3,050,373 or U.S. Pat. No. 3,061,523, for example. This is generally called an analytical test paper or simply a test piece and fluid sample is dropped on a test piece or a test piece is dipped in a fluid sample and a color change or an optical density change on the test piece is checked visually or measured with a reflecting densitometer, thus a density level of specific component in the fluid sample is determined.

These test pieces are useful because they are handy and provide a immediate result but due to their structure, they can not lie outside the region of a semi-quantitative analysis or a qualitative analysis.

In contrast with the conventional analyzing method like the foregoing, on the other hand, there is known a multi-layer analytical element which employs a handy dry chemistry and yet provides a high quantitativeness. For example, multi-layer analytical elements are disclosed in Japanese Patent Examined Publication No. 21677/1978, Japanese Patent Publication Open to Public Inspection Nos. 164,356/1980, 125,847/1982, 197,466/1982 and 90167/1983.

According to the elements described in aforesaid documents, all of the reagents used for analytical reactions are contained in a sheet of analytical element and blood serum or complete blood in a certain amount is dropped on aforesaid element which is then kept at a certain temperature for a certain period of time and then the reflecting density on the element is measured from the support side, thus it is possible to determine the substance concentration from aforesaid reflecting density.

Aforesaid method is far excellent in the accuracy of analysis compared with the conventional one of a test paper type and owns an efficiency higher than that of wet chemistry without preparing reagent in advance.

In the analytical element employing such dry chemistry, however, it is very difficult to cause the analytical element to contain enzyme that catalyzes a reaction system necessary for measuring an object to be tested, keeping the activity of aforesaid enzyme.

SUMMARY OF THE INVENTION

An object of the present invention is to provide an analytical element wherein the activity of enzyme is maintained as described above.

Aforesaid object is attained by an analytical element for analyzing a specific component aimed in advance in a fluid, aforesaid analytical element comprising at least one reagent-containing layer on a support and a spreading layer having a porous structure on the reagent-containing layer, wherein an enzyme necessary for the reaction to produce a product capable of detecting aforesaid specific component is caused to be contained in aforesaid porous spreading layer as a mixture with a protein and/or polypeptide compound being free from a substance which substantially disturbs aforesaid analysis and reaction.

In the analytical element of the present invention, the preservation stability of enzyme has greatly been improved and no ununiform color forming is observed. Therefore, it is possible to use the analytical element for the simple and prompt quantitative analysis for fluid samples, especially for the highly accurate dry type quantitative analysis of a component in a biological fluid sample, which is extremely advantageous practically.

DETAILED DESCRIPTION OF THE PREFERRED EMBODIMENTS

An analytical element of the present invention is prepared in a way wherein at least one reagent-containing layer containing at least one kind of reagent that reacts on the component in a fluid sample and comprising hydrophilic colloid is provided on a support and a spreading layer that causes the component in aforesaid fluid sample to be transmitted to aforesaid reagent-containing layer is put on aforesaid reagent-containing layer.

When analyzing, a fluid to be tested dropped on the analytical element transmits the spreading layer and reaches, while spreading through the spreading layer, the reagent-containing layer where the fluid to be tested reacts on reagent in the reagent-containing layer for the detection, thus a specific component may be detected.

When a specific component to be detected is a substance having a high hydrophobicity or when the specific component has a large molecular weight and thereby is unable to disperse through a hydrophilic polymer matrix such as a reagent-containing layer, it is desirable to change the substance to a detectable substance capable of dispersing through the reagent-containing layer containing hydrophilic polymers and of reacting for detection before aforesaid substance reaches the reagent-containing layer. For the aforesaid reason, an enzyme which serves as a catalyzer necessary for causing the reaction that changes aforesaid specific substance having a low dispersibility to a detectable substance is used.

Examples of such reaction are as follows.

When analyzing cholesterol, for example, the reactions for the mixture of cholesterol ester and cholesterol which is known to be existing in blood take place through the following steps.

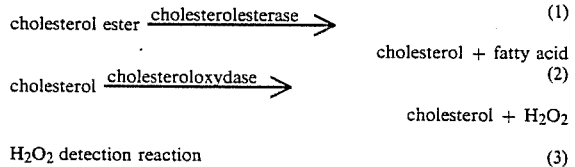

$$\text{cholesterol ester} \xrightarrow{\text{cholesterolesterase}} \quad (1)$$
$$\text{cholesterol + fatty acid}$$
$$\text{cholesterol} \xrightarrow{\text{cholesteroloxydase}} \quad (2)$$
$$\text{cholesterol + H}_2\text{O}_2$$

H₂O₂ detection reaction (3)

For the reactions of (1) and (2) above, enzyme, namely, cholesterolesterase and cholesteroloxydase are used. As an another example, the following reaction wherein lipase is used as an enzyme is given.

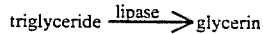

$$\text{triglyceride} \xrightarrow{\text{lipase}} \text{glycerin}$$

As stated above, various kinds of enzymes are used depending on the kinds of substances to be detected and it is preferable that those enzymes are contained in the spreading layer through which the fluid to be tested passes and aforesaid reactions take place before the fluid to be tested reaches a reagent-containing layer.

In order to form an enzyme-containing spreading layer, it is preferable to coat the layer with water or an aqueous medium. However, if aforesaid method is used, the movement of water-soluble reagent from a reagent-containing layer is induced, thereby it is impossible to attain a sufficient analyzing capability. For solving this problem, it is recommendable that aforesaid layer is coated with nonaqueous solvent but if, in that case, enzyme is dispersed and contained directly in the layer, denaturation deactivation of enzyme caused by nonaqueous solvent is induced and thereby the sensitivity of the analytical element drops remarkably.

In order to solve aforesaid problems, protein and/or polypeptide compound containing no disturbing substance are used in the present invention.

'Protein and/or polypeptide compound free from the substance which substantially disturbs aforesaid analysis and aforesaid reaction' used in the present invention means protein and/or polypeptide compound which does not substantially contain a specific component to be analyzed and enzyme activity and does not contain the substance that substantially disturb the reaction deriving aforesaid specific component to the detectable substance.

As a substance inhibiting aforesaid reaction, inhibiting agent for enzymes and undesirable activator are given. As an inhibiting agent, a heavy metal is well-known in general and it depends upon a type of enzymes.

Examples of above-defined protein and/or polypeptide compound preferably include albumin (bovine blood serum albumin, egg albumin etc.), globulin, gelatin and gelatin-decomposed-substance etc. As an enzyme necessary for deriving a specific component to a detectable substance, there may be given hydrolysis enzyme such as cholesterolesterase, lipoprotein lipase or the like, oxidized enzyme such as cholesteroloxydase, glucoseoxydase, peroxydase or the like, uricase, diaphorase, glutamic dehydrogenase and others. As an enzyme preferably contained in a porous spreading layer for the purpose of converting the substance to be tested to a substance diffusible through a reagent-containing layer comprising hydrophilic binders, cholesterolesterase, lipoprotein lipase, cholesteroloxydase and others are given. As for the ratio of aforesaid enzyme to protein and/or polypeptide compound free from disturbing substance, the range from 0.5 U to 100,000 U of enzyme for 1 g of protein and/or polypeptide is preferable and the ratio by weight ranging from 10:1 to 1:5000 is preferable and it is especially preferable to use within a range from 1:1 to 1:200. An amount of the enzyme contained in the spreading layer is preferable to be within the range from 10 to 100,000 U/m².

The porous spreading layer of the present invention has a capability (1) to distribute uniformly a certain amount of fluid sample in the reagent-containing layer per unit area thereof. It is further desirable that the porous spreading layer has a capability (2) for eliminating a substance or a cause to inhibit an analysis reaction in the fluid sample and/or a capability (3) to perform a background function for reflecting the light for measurement transmitted through the support when conducting a spectrophotometric analysis, in addition to aforesaid capability (1). Therefore, the porous spreading layer of the present invention can be either a layer having aforesaid capability (1) or a layer having, in addition to the capability (1), the capability (2) and/or (3), or it is possible to separate plural capabilities including the capability (1) and to use a separate layer for each capability. Further it is possible to use in combination the layer having two capabilities among aforesaid (1), (2) and (3) capabilities and the layer having one remaining capability. For example, a spreading layer of nonfibrous and porous medium composed of titanium dioxide and cellulose diacetate and called a brush polymer described in U.S. Pat. No. 3,992,158, a spreading layer of textile treated to be hydrophilic described in Japanese Patent O.P.I. Publication No. 164,356/1980, a spreading layer in Japanese Patent O.P.I. Publication Nos. 94658/1982, 125,847/1982, 197,466/1982 and 70161/1983, a spreading layer composed of dispersed fiber and reactive high polymer compound described in U.S. Pat. No. 4,427,632 and a spreading layer of a structure of combined particles described in U.S. Pat. No. 4,430,436 and Japanese Patent O.P.I. Publication No. 101,760/1982 are given. Especially, aforesaid spreading layer of a fibrous structure and the layer of a structure of combined particles are useful as a material capable of transmitting rapidly corpuscles. The thickness of a spreading layer in the analytical element of the invention should be determined according to the void ratio thereof and it preferably is from about 100 μm to 500 μm and more preferably is from about 150 μm to 350 μm. It is preferable that the void ratio is from about 20% to about 85%. In order to cause a porous spreading layer as the one described above to be contained with enzyme and protein and/or polypeptide compound of the invention, it is preferable to use the aforesaid mixture as a freeze-dried product. Freeze-dried products of aforesaid mixture are prepared in a way wherein enzyme and protein or polypeptide that does not detract the activity of the enzyme both to be freeze-dried are dissolved in distilled water or in a proper buffer solution and then aforesaid solution is frozen by liquid nitrogen or the like and then solvent is removed therefrom by a freeze drier, thus freeze-dried products are made. The freeze-dried products thus obtained can be used as they are, or after being powdered to fine pieces. Aforesaid porous spreading layer includes the one wherein porous materials prepared in advance such as textile or the like for example are attached on the support and the one wherein a coating solution such as the one in which fibers are dispersed in nonaqueous solvent solution of binder is coated on the support and following method, for example, may be employed for causing freeze-dried products of aforesaid mixture of enzyme and protein and/or polypeptide compound to be contained in aforesaid layers.

When forming with coating, aforesaid freeze-dried products are to be added at the optimum step in the preparation of the coating solution and to be dispersed uniformly in the coating solution through the physical method such as stirring or irradiation of supersonic waves or the like and then to be coated and dried in an ordinary method.

When using a substance which is originally porous such as a membrane filter, freeze-dried products are to be dispersed in a nonaqueous solvent through a known method and then the dispersion solution thus obtained is to be contained in the textile and others.

As an organic solvent for forming a porous spreading layer contained dispersively with a mixture of enzyme and protein and/or polypeptide compound, there may be given, for example, nonaqueous solvent such as xylene, benzene, toluene, methanol, ethanol, butanol, acetone, chloroform, tetrahydrofuran and others and what is preferable among them is a water unmiscible organic solvent such as xylene, benzene, toluene, butanol, chloroform and others.

When using peroxydase, hydrogen donor and coupler are to be used in combination according to an ordinary method.

As an example of hydrogen donor, there may be given 4-substituted antipyrine disclosed in Japanese Patent Publication Open to Public Inspection No. 52158/1973 (hereinafter referred to as Japanese Patent O.P.I. Publication), 2-hydrazonobenzthiazoline disclosed in Japanese Patent O.P.I. Publication No. 20471/1980, p-halogenophenol (see Japanese Patent O.P.I. Publication No. 174,099/1982) disclosed in Japanese Patent O.P.I. Publication No. 148,100/1980 and further o- or p- phenylenediamine group compound disclosed in Japanese Patent O.P.I. Publication Nos. 137,192/1975, 94653/1982 and 174,099/1982.

Preferable ones among the foregoing include 4-substituted antipyrine and p-phenylenediamine group compound, while 4-aminoantipyrine and p-phenylenediamine group compound shown as a concrete example in Japanese Patent O.P.I. Publication No. 94653/1982 are preferable in particular.

Hydrogen doners may be used within a broadly-selected amount and they may be used within a range from 0.01 milli mol/m$^2$ to 100 milli mol/m$^2$, preferably within a range from 0.05 to 50 milli mol/m$^2$.

As an example of a coupler, acylacetamido compound disclosed in Japanese Patent O.P.I. Publication No. 94654/1982, pyrazolone group compound disclosed in Japanese Patent O.P.I. Publication Nos. 94656/1982 and 174,099/1982, phenol group compound disclosed in Japanese Patent O.P.I. Publication Nos. 94653/1982 and 174,099/1982, naphthol group compound disclosed in Japanese Patent O.P.I. Publication Nos. 94655/1982 and 174,099/1982 and N,N-di substituted aniline compound disclosed in Japanese Patent O.P.I. Publication No. 174,099/1982 are given. Preferable ones among them are pyrazolone group compound, phenol group compound and naphthol group compound and, in particular, compounds shown as an actual example in Japanese Patent O.P.I. Publication Nos. 94656/1982, 94653/1982, 94655/1982 and 174,099/1982 and 2-tetrafluoroethylcarbonylamino-5-[α-(2,4-di-t-amylphenoxy)pentylcarbonylamino]phenol are preferable.

Couplers may be used within a widely-selected amount and the range is from 0.1 to 100 milli mol/m$^2$, preferably from 0.5 to 50 milli mol/m$^2$.

A support to be used in the invention is allowed to be the one which is widely-known and preferable one is fluid-impermeable and light-transmissible and examples thereof are various kinds of polymers such as cellulose acetate, polyethyleneterephthalate, polycarbonate or polystyrene. Further, in addition to aforesaid polymer materials, inorganic materials such as glass may similarly be used. The thickness of a support used in the invention is allowed to be any value but the range from about 50 μm to about 250 μm is preferable. It is further possible to give any processing to one surface at observation side of the support according to the purpose. Further, it is possible to improve the adhesiveness between the reagent-containing layer and the support by using the light-permeable subbing layer, at need, on the side of the support where the reagent-containing layer is provided.

As the other additional additive, various kinds of additives such as a preserver, a buffer, a surfactant and others, for example, may be added at need.

A surface active agent, in particular, may effectively be used for controlling the permeating speed when fluid samples are applied to the element of the present invention.

As a usable surface active agent, both ionic or (anionic or cationic) and non-ionic one may be used but non-ionic surfactant is effective. As an example of a non-ionic surfactant, polyalkyleneglycol derivative of alkyl substituted phenol such as 2,5-di-t-butylphenoxypolyethyleneglycol, p-octylphenoxypolyethyleneglycol and p-iso-nonylphenoxypolyethyleneglycol as well as polyalkyleneglycolester of higher fatty acid are given. These surfactants have an effect to control the speed of a fluid sample for permeating to the receptor layer and to inhibit concurrently the occurrence of undesirable 'chromatography phenomenon'.

Aforesaid surfactant may be used in an amount widely selected and the usable ratio thereof to the weight of coating solution is from 10% by weight to 0.005% by weight and preferably from 6% by weight to 0.05% by weight.

The reagent-containing layer of the invention is composed of a hydrophilic binder and it is also possible that two or more separate layers are provided.

As a binder, a gelatin, a gelatin derivative such as phthalic gelatin, a water-soluble cellulose derivative such as hydroxyethyl cellulose and carboxymethylcellulose sodium salt or the like, polyvinyl alcohol, polyacrylamide, polymethacrylamide, poly(mono or dialkyl-substituted)methacrylamide and water-soluble copolymer of the foregoing and others are given.

The analytical element of the invention may take, for the object of the invention, any combination of following layers and a member: a reflection layer and a subbing layer described in U.S. Pat. No. 3,992,158, a radiation-blocking layer described in U.S. Pat. No. 4,042,335, a barrier layer described in U.S. Pat. No. 4,066,403, a migration-prevention layer described in U.S. Pat. No. 4,166,093, a scavenger layer described in Japanese Patent O.P.I. Publication No. 90859/1980 and a destructive pod-shaped member described in U.S. Pat. No. 4,110,079.

Aforesaid various kinds of layers of an analytical element may be prepared in any thickness on the support of the invention according to its desirable structure by selecting and using a slide hopper coating method, an extrusion coating method, a dip coating method and others all of which have been known in the photo industry.

By the use of the analytical element of the invention, an amount of a specific component in a fluid sample may be measured from the side of the support of the invention through a reflection spectrophotometry in accordance with an initial speed method or a reaction termination method. The measured value thus obtained enables an amount of a specific component to be determined by being compared with the calibration curve.

An amount of a fluid sample to be applied to the analytical element of the invention is allowed to be determined at any value but the preferable amount is from about 5 μl to about 50 μl and more preferable one is from 5 μl to 20 μl. It is generally desirable to use about 10 μl of a fluid sample.

The analytical element of the invention may be used without any problem for the analysis of any of whole blood, blood serum and blood plasma. It may further be used without any problem for other body fluids such as urine, lymph, cerebrospinal fluid and others. When using whole blood, aforesaid radiation-blocking layer or other reflection layer may be provided at need to prevent the radiation for detection from being disturbed by blood corpuscles.

The analytical reaction used for the analytical element of the invention may freely be determined in accordance with its purpose and the analytical element is useful in the field of clinical chemistry, for example, and it is used especially for the analysis of the component in biological body fluid samples such as blood or urine.

EXAMPLES

The present invention will be explained more concretely as follows referring to the examples to which the invention is not limited.

Incidentally, in each example, the reagent-containing layer was prepared in a way wherein an aqueous solution prepared was coated.

EXAMPLE 1

One or two reagent-containing layers having the composition shown in Table-1 were provided on the subbed clear polyethyleneterephthalate support of 180 μm thick and then each material having the composition shown in Table-2 was coated on each reagent-containing layer as a spreading layer through a xylene dispersion method or an aqueous dissolution method, thus analytical elements 1 and 2 of the present invention shown in Table-3 and comparative analytical elements 1 and 2 also shown in Table-3 were prepared.

In order to test the capability of aforesaid samples of analytical element at the point immediately after the preparation thereof and the point after preservation at 40° C. for 10 days, serums (made by Lipid Serum Eiken-Kagaku Co.) containing cholesterolester in the amount of 100 mg/dl, 200 mg/dl, 400 mg/dl and 500 mg/dl respectively were dropped in the amount of 10 μl each on all of the samples. The test was carried out with 3 pieces of the same samples respecting. After allowing them to be kept at 37° C. for 10 minutes, the reflection density at 540 nm on the colored spot for each sample was measured by SAKURA Densitometer PDA-65 (made by Konishiroku Photo Ind. Co., Ltd.). The results thereof are shown in

TABLE 1

| | reagent-containing layer | | |
|---|---|---|---|
| | R-1 | R-2*[1] | R-3 |
| dipotassium hydrogenphosphate (g/m$^2$) | 3.3 | — | 3.3 |
| potassium dihydrogenphosphate (g/m$^2$) | 1.5 | — | 1.5 |
| 4-amino antipyrine (g/m$^2$) | — | 1.1 | 1.1 |
| 1,7-dihydroxynaphthalene (g/m$^2$) | 1.0 | — | 1.0 |
| dimedone (g/m$^2$) | 0.3 | — | 0.3 |
| peroxydase (U/m$^2$) | 5,000 | — | — |
| gelatin (g/m$^2$) | 25 | — | 25 |
| polyvinylpyrrolidone (g/m$^2$) | — | 5 | — |
| sodium triisopropylnaphthalene sulfonate (g/m$^2$) | 0.5 | — | 0.5 |
| 1,2-bis(vinylsulfonyl)ethane (g/m$^2$) | 0.2 | — | 0.2 |

*[1] A reagent-containing layer marked with 'R-2' was prepared by coating n-butanol solution.

TABLE 2

| | spreading layer | |
|---|---|---|
| | S-1 | S-2 |
| filter paper powder (made by Toyo Roshi Co., 300 mesh and over) (g/m$^2$) | 91 | 91 |
| styrene-glycidylmethacrylate copolymer (ratio by weight 9:1) (g/m$^2$) | 13 | 13 |
| p-octylphenoxypolyethoxyethanol (g/m$^2$) | 9 | 9 |
| cholesterolesterase (U/m$^2$) | 6,000*[2] | 6,000*[2] |
| cholesteroloxydase (U/m$^2$) | 6,000*[2] | 6,000*[2] |
| peroxydase (U/m$^2$) | — | 5,000 |
| Bovine serum albumin (g/m$^{3.8*}$) | 3.8*[2] | 3.8$^2$ |

*[2] Cholesterolesterase in the amount of 240 mg (25 U/mg) 75 mg (80 U/mg) of cholesteroloxydase and 3.8 g of serum albumin of cattle were dissolved in 100 ml of distilled water and then frozen and dried after being stirred unformly, thus freeze-dried powder of enzyme-serum albumin of cattle was prepared and then sieved with a 200 mesh sieve to be used.

TABLE 3

| analytical element No. | reagent-containing layer | | spreading layer | coating solvent for spreading layer |
|---|---|---|---|---|
| | reagent-containing layer-I | reagent-containing layer-II | | |
| analytical element of the invention-1 | R-1 | R-2 | S-1 | xylene |
| analytical | R-3 | — | S-2 | |

TABLE 3-continued

| analytical element No. | reagent-containing layer | | spreading layer | coating solvent for spreading layer |
|---|---|---|---|---|
| | reagent-containing layer-I | reagent-containing layer-II | | |
| element of the invention-2 | | | | |
| comparative analytical element-1 | R-1 | R-2 | S-1 | water |
| comparative analytical element-2 | R-3 | — | S-2 | |

TABLE 4

| cholesterol concentration (mg/dl) | instant | | | | 10 days later | | | |
|---|---|---|---|---|---|---|---|---|
| | 100 | 200 | 400 | 500 | 100 | 200 | 400 | 500 |
| analytical element of the invention-1 | 0.70 | 1.05 | 1.40 | 1.55 | 0.68 | 1.05 | 1.41 | 1.53 |
| | 0.70 | 1.06 | 1.39 | 1.56 | 0.69 | 1.05 | 1.37 | 1.54 |
| | 0.71 | 1.06 | 1.41 | 1.54 | 0.69 | 1.03 | 1.37 | 1.51 |
| analytical element of the invention-2 | 0.68 | 1.06 | 1.43 | 1.56 | 0.69 | 1.02 | 1.40 | 1.52 |
| | 0.69 | 1.09 | 1.43 | 1.58 | 0.71 | 1.05 | 1.42 | 1.50 |
| | 0.70 | 1.08 | 1.41 | 1.57 | 0.72 | 1.04 | 1.39 | 1.49 |
| comparative analytical element-1 | 0.63 | 0.98 | 1.30 | 1.39 | 0.50 | 0.55 | 0.71 | 1.01 |
| | 0.71 | 1.09 | 1.45 | 1.50 | 0.59 | 0.67 | 0.61 | 0.60 |
| | 0.76 | 1.01 | 1.39 | 1.41 | 0.37 | 0.39 | 0.56 | 0.59 |
| comparative analytical element-2 | 0.60 | 0.96 | 1.31 | 1.36 | 0.30 | 0.51 | 0.55 | 1.12 |
| | 0.75 | 1.08 | 1.46 | 1.53 | 0.58 | 0.40 | 0.71 | 0.58 |
| | 0.72 | 1.00 | 1.38 | 1.41 | 0.39 | 0.58 | 0.61 | 0.60 |

As is clear from Table-4, a considerable variation in reflection density value of the same samples and a deterioration in preservation were observed on the comparative analytical elements when serums of same concentration were dropped thereon, while on the analytical elements of the invention, the variation in reflection density value observed was small and on excellent capability for preservation was observed.

Further, the analytical elements of the invention showed no ununiform coloring compared with comparative analytical elements.

EXAMPLE 2

Two reagent-containing layers having the composition shown in Table-5 were provided on the subbed clear polyethylene-phthalate support of about 180 μm thick and then each material having the composition shown in Table-6 was coated on each reagent-containing layer as a spreading layer through a xylene dispersion method, thus an analytical element-1 (same as Example-1) of the invention shown in Table-7 as well as comparative analytical elements 3 and 4 also shown in Table-7 were prepared.

In order to test the capability of aforesaid samples of analytical element at the point immediately after the preparation thereof and the point after preservation at 40° C. for 10 days, serums (made by Lipid Serum Eiken-Kagaku Co.) containing cholesterolester in the amount of 100 mg/dl, 200 mg/dl, 400 mg/dl and 500 mg/dl respectively were dropped in the amount of 10 μl each on all of the samples. After allowing them to be kept at 37° C. for 10 minutes, the reflection density at 540 nm on the colored spot for each sample was measured by SAKURA Densitometer PDA-65 (made by Konishiroku Photo Ind. Co., Ltd.). As a result, in the same way as what was shown in Example 1, comparative analytical elements showed a low discriminating ability when serums of aforesaid respective densities were dropped thereon and also showed a deterioration in preservation, while the analytical element of the invention showed an excellent discriminating ability and preservability.

TABLE 5

| | reagent-containing layer | | |
|---|---|---|---|
| | R-1 | R-2 | R-3 |
| dipotassium hydrogenphosphate ($g/m^2$) | 3.3 | — | 3.3 |
| potassium dihydrogenphosphate ($g/m^2$) | 1.5 | — | 1.5 |
| 4-amino antipyrine ($g/m^2$) | — | 1.1 | — |
| 1,7-dihydroxynaphthalene ($g/m^2$) | 1.0 | — | 1.0 |
| dimedone ($g/m^2$) | 0.3 | — | 0.3 |
| peroxydase ($U/m^2$) | 5,000 | — | 5,000 |
| cholesterolesterase ($U/m^2$) | — | — | 6,000 |
| cholesteroloxydase ($U/m^2$) | — | — | 6,000 |
| gelatin ($g/m^2$) | 25 | — | 25 |
| polyvinylpyrrolidone ($g/m^2$) | — | 5 | — |
| sodium triisopropylnaphthalene sulfonate ($g/m^2$) | 0.5 | — | 0.5 |
| 1,2-bis(vinylsulfonyl)ethane ($g/m^2$) | 0.2 | — | 0.2 |

TABLE 6

| | spreading layer | | |
|---|---|---|---|
| | S-1 | S-2 | S-3 |
| filter paper powder (made by Toyo Roshi Co., 300 mesh and over) ($g/m^2$) | 91 | 91 | 91 |
| styrene-glycidylmethacrylate copolymer (ratio by weight 9:1) ($g/m^2$) | 13 | 13 | 13 |
| p-octylphenoxypolyethoxyethanol ($g/m^2$) | 9 | 9 | 9 |
| cholesterolesterase ($U/m^2$) | 6,000*2 | 6,000 | — |
| cholesteroloxydase ($U/m^2$) | 6,000*2 | 6,000 | — |
| Bovine serum albumin ($g/m^2$) | 3.8*2 | — | — |

*2See *2 of Table-2.

TABLE 7

| analytical element No. | reagent-containing layer | | spreading layer |
|---|---|---|---|
| | reagent-containing layer-I | reagent-containing layer-II | |
| analytical element of the invention-1 | R-1 | R-2 | S-1 |
| comparative analytical element-3 | R-1 | R-2 | S-3 |
| comparative analytical element-4 | R-4 | R-2 | S-4 |

EXAMPLE 3

Two reagent-containing layers having the composition shown in Table-8 were provided on the clear and subbed polyethylenephthalate support of about 180 μm thick and then each material having the composition shown in Table-9 was coated on each reagent-containing layer as a spreading layer through a xylene dispersion method, thus an analytical element-3 of the invention and a comparative analytical elements 5 both shown in Table-10 were prepared.

In order to test the capability of aforesaid samples of analytical element at the point immediately after the preparation thereof and the point after preservation at 40° C. for 10 days, serums (made by Lipid Serum Eiken-Kagaku Co.) containing triglyceride in the amount of 100 mg/dl, 200 mg/dl and 300 mg/dl respectively were dropped in the amount of 10 μl each on all of the samples. After allowing them to be kept at 37° C. for 10 minutes, the reflection density at 540 nm on the colored spot for each sample was measured by SAKURA Densitometer PDA-65 (made by Konishiroku Photo Ind. Co., Ltd.). As shown in Table-11, in the same way as what was shown in Example 1, a comparative analytical element showed a low discriminating ability when serums of aforesaid respective densities were dropped thereon and also showed a deterioration in preservation, while the analytical element of the invention showed an excellent discriminating ability and preservability.

TABLE 8

|  | reagent-containing layer | |
|---|---|---|
|  | R-5 | R-6 |
| sodium carbonate (g/m$^2$) | — | 7.5 |
| cyclohexylaminopropane sulfonic acid (g/m$^2$) | 6.5 | — |
| neotetrazolium blue (g/m$^2$) | 0.8 | — |
| diaphorase (U/m$^2$) | 2,100 | — |
| glyceroldehydrogenase (U/m$^2$) | 20,000 | — |
| gelatin (g/m$^2$) | 25 | — |
| polyvinylpyrrolidone (g/m$^2$) | — | 6 |
| p-octylphenoxypolyethoxyethanol (g/m$^2$) | 0.1 | 0.1 |
| 1,2-bis(vinylsulfonyl)ethane (g/m$^2$) | 0.1 | — |

TABLE 9

|  | spreading layer | |
|---|---|---|
|  | S-5 | S-6 |
| filter paper powder (made by Toyo Roshi Co., 300 mesh and over) (g/m$^2$) | 91 | 91 |
| styrene-glycidylmethacrylate copolymer (ratio by weight 9:1) (g/m$^2$) | 13 | 13 |
| p-octylphenoxypolyethoxyethanol (g/m$^2$) | 9 | 9 |
| lipoprotein lipase (U/m$^2$) | 8,000*$^3$ | 8,000 |
| Bovine serum albumin (g/m$^2$) | 3.8*$^3$ | — |

*$^3$Lipoprotein lipase in the amount of 800 mg (10 U/mg), and 3.8 g of serum albumin of cattle were dissolved in 100 ml of distilled water and then frozen and dried after being stirred uniformly, thus freeze-dried powder of enzyme-bovin serum albumin of cattle was prepared and then sieved with a 200 mesh sieve to be used.

TABLE 10

| analytical element No. | reagent-containing layer-I | reagent-containing layer-II | spreading layer |
|---|---|---|---|
| containing element of the invention-3 | R-5 | R-6 | S-5 |
| comparative analytical element-5 | R-5 | R-6 | S-6 |

TABLE-11

| number of days for preservation | instant | | | 10 days later | | |
|---|---|---|---|---|---|---|
| concentration of triglyceride (mg/dl) | 100 | 200 | 300 | 100 | 200 | 300 |
| analytical element of the invention-3 | 0.82 | 1.10 | 1.33 | 0.84 | 1.09 | 1.30 |
| comparative analytical element-5 | 0.84 | 1.08 | 1.28 | 0.80 | 0.87 | 0.91 |

EXAMPLE 4

A reagent-containing layer 'R-1' among those shown in Table-5 was first provided and then 'R-2' layer thereof was provided on a clear and subbed polyethyleneterephthalate support of about 180 μm thick. Then the spreading layer prepared in a following method was attached thereon with a light pressure and on this layer, 2,5-di-t-butylphenoxypolyethyleneglycol aqueous solution was further sprayed and dried, thus a film for analyzing cholesterol was prepared.

Method for Preparing a Spreading Layer

A broad cloth woven with a cotton thread of a yarn number count '60' (made by Nisshin Boseki Co.) was treated in an aqueous solution of 1% gelatin, thus a textile for the use treated to be hydrophilic and having a gelatin-containing percentage of 2.5% for the use of a spreading layer for fluid samples was prepared.

The mouth of a beaker was covered with aforesaid textile for spreading layer and thereon, the dispersion solution having the composition shown in Table-12 was poured. The textile for spreading layer having the dispersion solution sticking thereon was then put carefully in xylene in a small amount and was subjected to an ultrasonic dispersion for 10 minutes while being cooled. After that, it was subjected to an air drying at a room temperature, thus a textile for spreading layer having dispersed substances sticking thereon was obtained.

TABLE 12

| reagent | |
|---|---|
| Freeze-dried powder of bovine serum albumin containing cholesteroloxydase and cholesterolesterase | 4.2 g |
| xylene | 300 ml |

As a result, the analytical element of the invention showed an excellent discriminating power and preservability.

EXAMPLE 5

The reagent-containing layer was first provided in the same way as that in Example 4 and then the spreading layer prepared in the following preparing method was further attached on aforesaid reagent-containing layer with a light pressure. This was sprayed with a 2,5-di-t-butylphenoxypolyethyleneglycol aqueous solution and then dried, thus a element for analyzing cholesterol was prepared.

Method for Preparing a Spreading Layer

A filter paper (No. 7 made by Toyo Roshi Co.) was dipped in a uniform dispersion solution having the composition shown in Table-13 and was subjected to an ultrasonic dispersion for 15 minutes while being cooled and then was subjected to an air drying at a room temperature, thus a filter paper for spreading layer having dispersed substances sticking thereon was prepared.

As a result, the analytical element of the invention showed an excellent discriminating ability and preservability.

TABLE 13

| reagent | |
|---|---|
| Freeze-dried powder of bovine serum albumin containing cholesteroloxydase and cholesterolesterase | 3.0 g |
| xylene | 200 ml |

EXAMPLE 6

A reagent-containing layer 'R-5' among those shown in Table-8 was first provided and then 'R-6' layer thereof was provided on a clear and subbed polyethyleneterephthalate support of about 180 μm thick. Then the cellulose filter paper prepared in a following method was attached thereon with a light pressure and on this layer, 2,5-di-t-butylphenoxypolyethyleneglycol aqueous solution was further sprayed and dried, thus a an element for analyzing triglyceride was prepared and used.

Method for Preparing a Cellulose Filter Paper for Spreading Layer

Lipoproteinlipase in the amount of 800 mg (10 U/mg) and 3.8 g of serum albumin of cattle were, while being cooled, dissolved in 100 ml of distilled water and were stirred uniformly and then frozen at −40° C. This was subjected to a freeze-drying under a vacuum and thus freeze-dried powder was prepared. A cellulose filter paper (for example, No. 3A made by Toyo Roshi Co.) washed fully with pure water was suspended in xylene and this was spreaded on a fine nylon mesh. After drying, the nylon mesh was peeled and thus a cellulose filter paper for spreading layer was prepared and used.

As a result, the analytical element of the invention showed an excellent discriminating ability and preservability.

What is claimed is:

1. An analytical element for the analysis of a specific component in a fluid, said element comprising:
   (a) a support,
   (b) a layer containing a reagent provided on said support,
   (c) a spreading layer provided on said reagent-containing layer, said spreading layer having a porous structure, and
   (d) a dispersion mixture contained in the porous structure of said spreading layer and including a mixture of an enzyme and a protein and/or polypeptide, formed by freeze-drying a mixture of said enzyme and said protein and/or said polypeptide from an aqueous solution thereof, said enzyme being of a type supporting a reaction with said specific component to produce a product capable of being detected with said reagent, and said protein and/or polypeptide being substantially free from a substance disturbing said reaction or analysis whereby the protein and/or polypeptide prevent rapid deterioration of the enzyme.

2. The analytical element of claim 1 wherein said enzyme is a hydrolase.

3. The analytical element of claim 2 wherein said hydrolase is a cholesterolesterase or a lipoproteinlipase.

4. The analytical element of claim 1 wherein said enzyme is an oxidizing enzyme.

5. The analytical element of claim 4 wherein said oxidizing enzyme is selected from the group consisting of cholesteroloxydase, glucoseoxydase, peroxydase and uricase.

6. The analytical element of claim 1 wherein said enzyme is a dehydrase.

7. The analytical element of claim 6 wherein said dehydrase is a diaphorase or a glutamic acid dehydrase.

8. The analytical element of claim 1 wherein an amount of said enzyme contained in said spreading layer is from 10 U/m$^2$ to 100,000 U/m$^2$ of said layer.

9. The analytical element of claim 1 wherein said protein or polypeptide compound is selected from the group consisting of albumin, globulin, gelatin and decomposed gelatin.

10. The analytical element of claim 1 wherein a proportion of the enzyme to the protein and/or the polypeptide compound is from 10:1 to 1:5000 by weight.

11. The analytical element of claim 9 wherein the proportion of the enzyme to the protein and/or the polypeptide compound is from 1:1 to 1:200 by weight.

12. The analytical element of claim 1 wherein said spreading layer comprises fibrous material.

13. The analytical element of claim 1 wherein said spreading layer comprises combined particles.

14. The analytical element of claim 1 wherein the thickness of said spreading layer is from about 100 to about 500 μm.

15. The analytical element of claim 14 wherein the thickness of said spreading layer is from about 150 to about 350 μm.

16. The analytical element of claim 1 wherein the porosity of said spreading layer is from about 20 to about 50%.

17. The analytical element of claim 8 wherein said protein or polypeptide compound is selected from the group consisting of albumin, globulin, gelatin and decomposed gelatin.

18. The analytical element of claim 17 wherein a proportion of the enzyme to the protein and/or the polypeptide compound is from 10:1 to 1:5000 by weight.

19. The analytical element of claim 18 wherein the proportion of the enzyme to the protein and/or the polypeptide compound is from 1:1 to 1:200 by weight.

20. The analytical element of claim 19 wherein thickness of said spreading layer is from about 100 to about 500 μm.

21. The analytical element of claim 20 wherein the thickness of said spreading layer is from about 150 to about 350 μm.

22. The analytical element of claim 21 wherein the porosity of said spreading layer is from about 20 to about 50%.

23. The analytical element of claim 17 wherein said enzyme is selected from the group consisting of hydrolase, oxidizing enzymes, and dehydrase.

* * * * *